United States Patent
Tachikawa

(10) Patent No.: US 10,098,536 B2
(45) Date of Patent: Oct. 16, 2018

(54) IMAGING APPARATUS, METHOD OF OPERATING AN IMAGING APPARATUS, INFORMATION PROCESSING APPARATUS, AND STORING MEDIUM

(71) Applicant: CANON KABUSHIKI KAISHA, Tokyo (JP)

(72) Inventor: Hiroto Tachikawa, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 265 days.

(21) Appl. No.: 15/134,587

(22) Filed: Apr. 21, 2016

(65) Prior Publication Data

US 2016/0321828 A1    Nov. 3, 2016

(30) Foreign Application Priority Data

May 1, 2015   (JP) ................................. 2015-093998

(51) Int. Cl.
    *A61B 3/10*   (2006.01)
(52) U.S. Cl.
    CPC .................... *A61B 3/102* (2013.01)
(58) Field of Classification Search
    CPC combination set(s) only.
    See application file for complete search history.

(56) References Cited

U.S. PATENT DOCUMENTS

| | | | |
|---|---|---|---|
| 8,721,078 B2 | 5/2014 | Torii et al. | |
| 9,750,404 B2 * | 9/2017 | Tachikawa | A61B 3/102 |
| 9,839,350 B2 * | 12/2017 | Naba | A61B 3/102 |
| 2011/0032479 A1 * | 2/2011 | Utsunomiya | A61B 3/0058 351/206 |
| 2011/0109913 A1 * | 5/2011 | Hacker | A61B 3/1005 356/482 |
| 2012/0140172 A1 | 6/2012 | Torii et al. | |
| 2012/0200859 A1 * | 8/2012 | Breitenstein | A61B 3/102 356/479 |
| 2012/0249769 A1 * | 10/2012 | Naba | A61B 3/102 348/78 |
| 2013/0004046 A1 * | 1/2013 | Nakano | A61B 3/102 382/131 |

(Continued)

FOREIGN PATENT DOCUMENTS

JP    2012-115578 A   6/2012

*Primary Examiner* — Avinash Yentrapati
(74) *Attorney, Agent, or Firm* — Fitzpatrick, Cella, Harper & Scinto

(57) ABSTRACT

Provided is an imaging apparatus, including: a light source which irradiates light that is frequency swept; an interference unit which diverges the irradiation light into irradiation light, which is to be irradiated on an object to be inspected, and reference light, to generate coherent light from reflected light of the irradiation light from the object to be inspected and the reference light; at least two conversion units which subject at least two analog signals, which are obtained by diverging an analog signal of the coherent light, to analog-to-digital conversion; an association unit which associates indices of at least two data arrays obtained by the analog-to-digital conversion; an integration unit which integrates the at least two data arrays based on the associated indices; and an image generating unit which generates an image of the object to be inspected based on a data array obtained by the integration.

20 Claims, 9 Drawing Sheets

(56) References Cited

U.S. PATENT DOCUMENTS

| | | | |
|---|---|---|---|
| 2013/0016320 A1* | 1/2013 | Naba | A61B 3/102 |
| | | | 351/208 |
| 2014/0024930 A1* | 1/2014 | Furuichi | A61B 5/6852 |
| | | | 600/424 |
| 2014/0340634 A1* | 11/2014 | Kuranov | A61B 3/102 |
| | | | 351/206 |
| 2015/0305617 A1* | 10/2015 | Tachikawa | A61B 3/102 |
| | | | 351/206 |
| 2016/0054113 A1* | 2/2016 | Osawa | G01B 9/02083 |
| | | | 356/497 |
| 2016/0106316 A1* | 4/2016 | Tachikawa | A61B 3/152 |
| | | | 351/208 |
| 2016/0166143 A1* | 6/2016 | Goto | A61B 3/0025 |
| | | | 351/206 |
| 2016/0317018 A1* | 11/2016 | Sakagawa | A61B 3/102 |
| 2017/0150900 A1* | 6/2017 | Furuichi | A61B 5/061 |

* cited by examiner

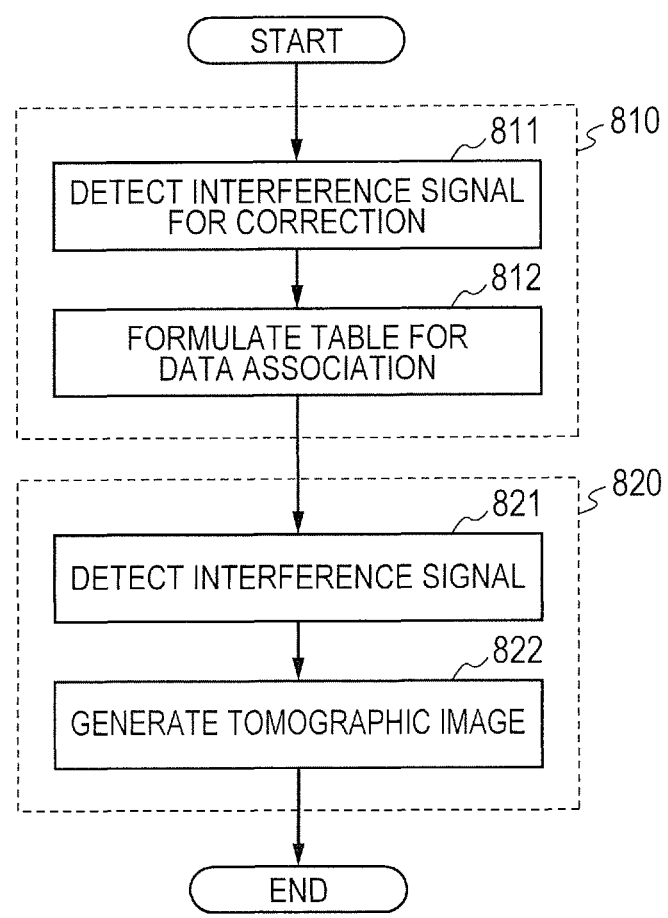

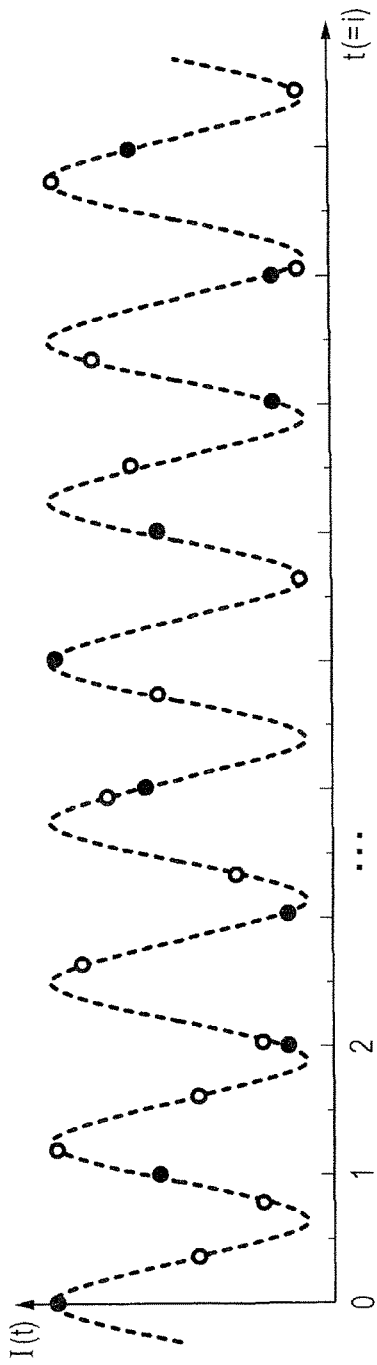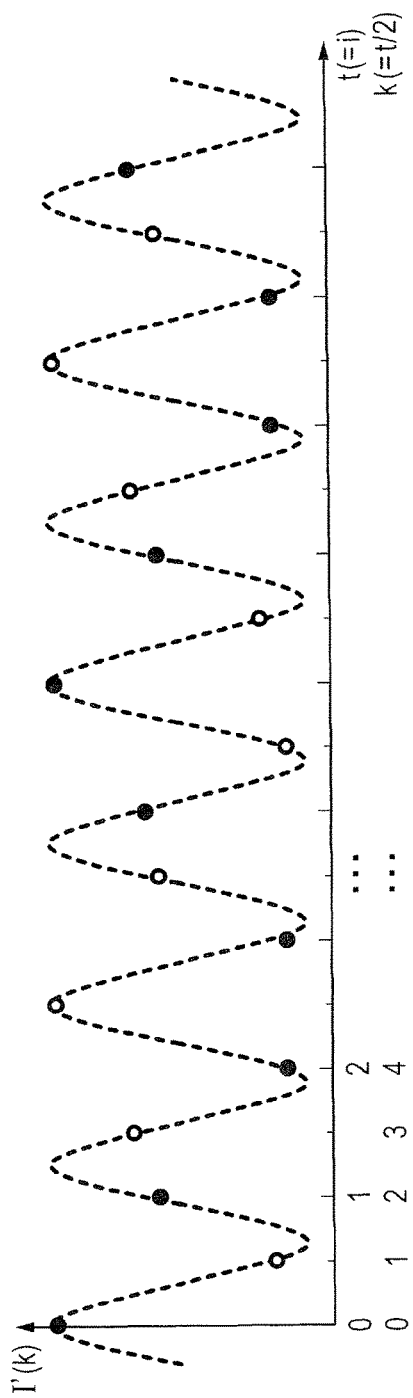

IMAGING APPARATUS, METHOD OF OPERATING AN IMAGING APPARATUS, INFORMATION PROCESSING APPARATUS, AND STORING MEDIUM

BACKGROUND OF THE INVENTION

Field of the Invention

The present invention relates to an imaging apparatus configured to acquire an optical coherence tomographic image, a method of operating the imaging apparatus, an information processing apparatus to be connected to the imaging apparatus, and a storing medium.

Description of the Related Art

An imaging apparatus employing optical coherence tomography which is hereinafter referred to as OCT and the imaging apparatus employing OCT which is hereinafter referred to as "OCT unit" has been developed (Japanese Patent Application Laid-Open No. 2012-115578). In the OCT unit, light is irradiated on an object while changing a wavelength of the irradiation light to cause interference between reflected light, which is obtained as the irradiation light returning from different depths of the object, and reference light corresponding to the irradiation light. Then, frequency components included in a time waveform of the strength of the coherent light (hereinafter abbreviated as "interference spectrum") is analyzed to obtain information on a section of the object, and more specifically, a tomographic image. Such an OCT unit is used in fundus inspection, for example.

Many ocular diseases are difficult to be completely cured, and hence it is important to discover a lesion of the fundus at an early stage, and to start treatment to delay the progress of the lesion extending over a wide area of the fundus at an early stage. In particular, a profound effect is exerted on a visual sense when the lesion reaches a macula, and hence there is a demand that the lesion be discovered even when the lesion exists at a position sufficiently distant from the macula. In order to satisfy the demand, the OCT apparatus used for the fundus inspection is expected to have a wider field angle.

As a technology to satisfy such expectation, in Japanese Patent Application Laid-Open No. 2012-115578, to widen an observation area of a tomographic image of a fundus, connecting a plurality of tomographic images to one another to form a tomographic image of a wide range is disclosed. In Japanese Patent Application Laid-Open No. 2012-115578, an OCT unit employing a variable wavelength light source (swept source OCT unit, hereinafter referred to as "SS-OCT unit") is also disclosed, and as the variable wavelength light source, a fiber ring resonator and a wavelength selective filter are exemplified.

However, in the method disclosed in Japanese Patent Application Laid-Open No. 2012-115578, image processing for sequentially connecting the acquired plurality of tomographic images is time-consuming and troublesome. Therefore, it is preferred to acquire the information on the section over the wide range in one image acquisition cycle. In this case, an eyeball is substantially spherical, and hence optical path lengths of the irradiation light significantly vary for a central portion and a peripheral portion of the fundus. Therefore, with the OCT unit having the structure of the related art, the information on the section cannot be obtained accurately over the wide range in some cases.

SUMMARY OF THE INVENTION

The present invention has been made to solve the above-mentioned problem, and therefore has an object to provide an imaging apparatus configured to accurately acquire information on a section even when a range of image acquisition in one scanning cycle is increased, a method of operating the imaging apparatus, an information processing apparatus to be connected to the imaging apparatus, and a storing medium.

In order to solve the above-mentioned problem, according to one embodiment of the present invention, there is provided an imaging apparatus, including:

a light source configured to irradiate light that is frequency swept;

an interference unit configured to diverge the irradiation light into irradiation light, which is to be irradiated on an object to be inspected, and reference light, to generate coherent light from reflected light of the irradiation light from the object to be inspected and the reference light;

at least two conversion units configured to subject at least two analog signals, which are obtained by diverging an analog signal of the coherent light, to analog-to-digital conversion;

an association unit configured to associate indices of at least two data arrays obtained by the analog-to-digital conversion;

an integration unit configured to integrate the at least two data arrays based on the associated indices; and an image generating unit configured to generate an image of the object to be inspected based on a data array obtained by the integration.

According to the present invention, the information on a section can be acquired accurately even when the range of image acquisition in one scanning cycle is increased.

Further features of the present invention will become apparent from the following description of exemplary embodiments with reference to the attached drawings.

BRIEF DESCRIPTION OF THE DRAWINGS

FIG. 9 is a chart for illustrating an overall flow from acquisition of data to generation of an image according to the second embodiment of the present invention.

FIGS. 10A and 10B are diagrams for each illustrating an equal wavenumber conversion process in the second embodiment of the present invention.

DESCRIPTION OF THE EMBODIMENTS

Now, embodiments of the present invention are described with reference to the drawings. In the following description, embodiment modes of an imaging apparatus are exemplified as the present invention, but may also be understood as examples of a method of operating the imaging apparatus. Note that, the following embodiments are not intended to limit the present invention in terms of the appended claims, and not all combinations of features described in the embodiments are necessarily required for solving means of the present invention. For example, an OCT unit according to the embodiments is formed of a Mach-Zehnder interferometer. However, the present invention is not limited thereto, and the OCT unit may be formed of a Michelson interferometer. Moreover, the OCT unit according to the embodiments is configured to change a reference optical path length. However, the present invention is not limited thereto, and the OCT unit may be configured to change a difference in optical path length between reference light and measurement light. For example, the OCT unit only needs to be configured so that the reference optical path length is fixed and a measurement optical path length is changed.

First Embodiment

Figure 1:
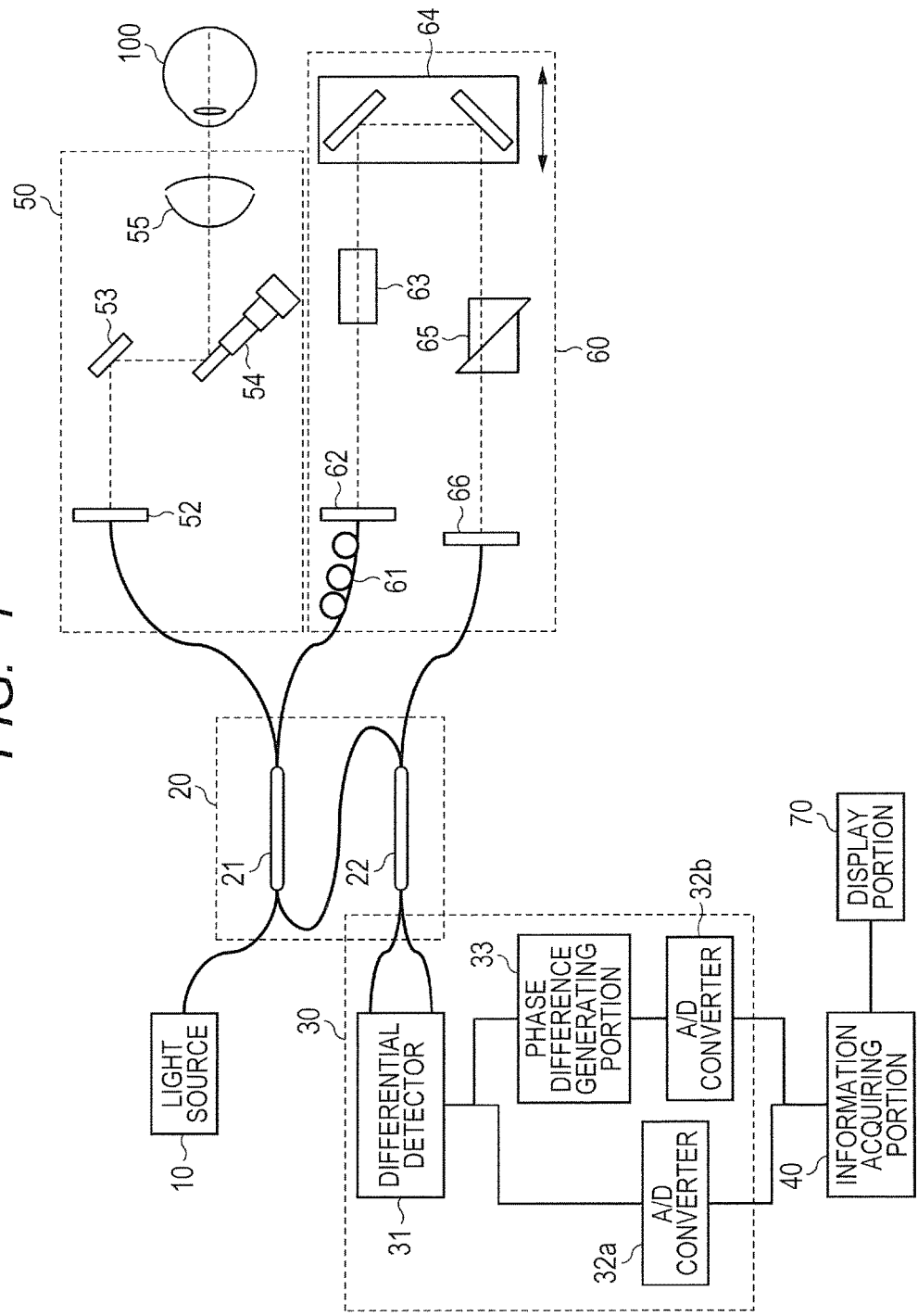
FIG. 1 is a schematic diagram for illustrating the schematic structure of an OCT unit according to a first embodiment of the present invention.

FIG. 1 is a schematic diagram for schematically illustrating a structure example of an imaging apparatus (OCT unit) employing optical coherence tomography according to a first embodiment of the present invention. The OCT unit includes a light source 10, an interference unit 20, a detecting portion 30, an information acquiring portion 40, a measurement arm 50, and a reference arm 60. Light irradiated from the light source 10 is frequency swept. The interference unit 20 is configured to generate coherent light based on reflected light, which is to be described below, and the reference light. The detecting portion 30 is configured to detect this coherent light. The information acquiring portion 40 is configured to acquire information on a fundus of an eye to be inspected 100 based on the detected coherent light.

The interference unit 20 and the measurement arm 50 are described. The interference unit 20 includes a coupler 21 and a coupler 22. The light source 10, the coupler 21, and the measurement arm 50 are connected via an optical fiber. The measurement arm 50 includes a collimator lens 52, an X-axis scanner 53, a Y-axis scanner 54, and a focus lens 55, which are arranged in the stated order from the coupler 21 side.

First, the coupler 21 is configured to diverge the light irradiated from the light source 10 into irradiation light, which is to be irradiated on the fundus, and the reference light. The irradiation light is irradiated on the eye to be inspected 100 via the measurement arm 50. More specifically, the irradiation light that has entered the measurement arm 50 is irradiated as spatial light from the collimator lens 52. Thereafter, the irradiation light is irradiated on the fundus of the eye to be inspected 100 via the X-axis scanner 53, the Y-axis scanner 54, and the focus lens 55. Each of the X-axis scanner 53 and the Y-axis scanner 54 is a scanning portion having a function of scanning the fundus with the irradiation light. A position at which the irradiation light is irradiated on the fundus is changed by the scanning portion. Then, back-scattered light (reflected light) from the fundus is irradiated from the measurement arm 50 again via the focus lens 55, the Y-axis scanner 54, the X-axis scanner 53, and the collimator lens 52. The reflected light that has been irradiated enters the coupler 22 via the coupler 21.

The reference arm 60 is described. The reference arm 60 is connected to the coupler 21 via an optical fiber. The reference arm 60 includes a collimator lens 62, a dispersion compensation glass 63, an optical path adjusting optical system 64, a dispersion adjusting prism pair 65, and a collimator lens 66, which are arranged in the stated order from the coupler 21 side.

The reference light is transmitted through the optical fiber to the reference arm 60, and enters the coupler 22 via the reference arm 60. More specifically, the reference light that has entered the reference arm 60 is adjusted in terms of a polarization state by a polarization controller 61, and then is irradiated as spatial light from the collimator lens 62. Thereafter, the reference light is transmitted through the dispersion compensation glass 63 to the optical path adjusting optical system 64. The optical path adjusting optical system 64 is configured to move in the direction of the arrow in the figure to adjust an optical path length of the reference light. The reference light that has passed through the optical path adjusting optical system 64 is transmitted through the dispersion adjusting prism pair 65, and enters an optical fiber via the collimator lens 66. The optical fiber is connected to the coupler 22, and the reference light irradiated from the reference arm 60 enters the coupler 22.

The coupler 22 is configured to multiplex the reflected light from the eye to be inspected 100 that has passed through the measurement arm 50 and the light that has passed through the reference arm 60 to generate the coherent light. Then, the coherent light is detected by the detecting portion 30. The detecting portion 30 includes a differential detector 31, a phase difference generating portion 33, and an A/D converter 32a and an A/D converter 32b, which are analog-to-digital conversion units.

In the detecting portion 30, each of the coherent light beams obtained by generating the coherent light in the coupler 22 and immediately thereafter demultiplexing the coherent light is detected by the differential detector 31. Then, an interference signal, which is an analog signal converted into an electrical signal by photoelectric conversion performed by the differential detector 31, is diverged again, and the diverged signals are respectively converted into digital signals by the A/D converter 32a and the A/D converter 32b. Sampling by each of the A/D converters 32a and 32b is performed at equal time intervals using an internal clock. The internal clock is included in each of the A/D converters 32a and 32b.

Between the differential detector 31 and the A/D converter 32b, the phase difference generating portion 33 configured to give a phase difference to the interference signals respectively acquired by the A/D converters 32a and 32b is arranged. The phase difference generating portion 33 is a coaxial cable, and is arranged to allow the A/D converter 32a and the A/D converter 32b to perform analog-to-digital conversion on the interference signal, which is the analog signal, at different times. Digital signals obtained by the respective converters are transmitted to the information acquiring portion 40. The information acquiring portion 40 is configured to perform frequency analysis such as Fourier transform on those digital signals to obtain the information on the fundus. The obtained information on the fundus is displayed as a tomographic image by a display portion 70.

The process of the acquisition of the information on a section at one point of the eye to be inspected 100 has been described above, and thus acquiring the information on a section in a depth direction of the eye to be inspected 100 is referred to as "A-scan". Moreover, acquiring information on a section of the eye to be inspected 100 in a direction orthogonal to the A-scan, that is, a two-dimensional image in the depth direction of the eye to be inspected 100 is referred to as "B-scan". Further, acquiring information in a direction orthogonal to the scanning directions of both of the A-scan and the B-scan is referred to as "C-scan". In other words, in two-dimensional raster scan performed along a surface of the fundus to acquire a three-dimensional tomographic image, a high-speed scanning direction corresponds to the B-scan, and a low-speed scanning direction in which scanning is performed by further performing the B-scan sequentially in the direction orthogonal to the B-scan corresponds to the C-scan. The A-scan and the B-scan may be performed to obtain a two-dimensional tomographic image, and the A-scan, the B-scan, and the C-scan may be performed to obtain the three-dimensional tomographic image. The B-scan and the C-scan are performed by scanning an irradiation position of the irradiation light with the above-mentioned X-axis scanner 53 and Y-axis scanner 54.

The X-axis scanner 53 and the Y-axis scanner 54 are formed of deflecting mirrors arranged so that axes of rotation are orthogonal to each other. The X-axis scanner 53 performs scanning in an X-axis direction, and the Y-axis scanner 54 performs scanning in a Y-axis direction. The directions of the "X-axis direction" and the "Y-axis direction" as used herein are directions perpendicular to an eye axis direction of an eyeball of the eye to be inspected 100, and are directions perpendicular to each other. Moreover, line scanning directions such as in the B-scan and the C-scan may not align with the X-axis direction or the Y-axis direction. Therefore, the line scanning directions of the B-scan and the C-scan may be determined as appropriate depending on the two-dimensional tomographic image or the three-dimensional tomographic image to be acquired.

Figure 2A:
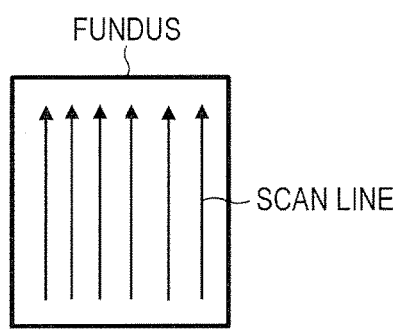
FIGS. 2A, 2B, 2C and 2D are schematic diagrams for illustrating examples of methods of scanning with irradiation light, which are performed by a scanning portion of the OCT unit.
Figure 2B:
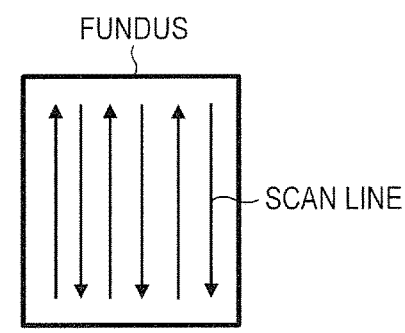
Figure 2C:
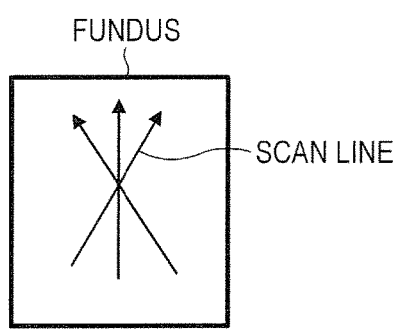
Figure 2D:
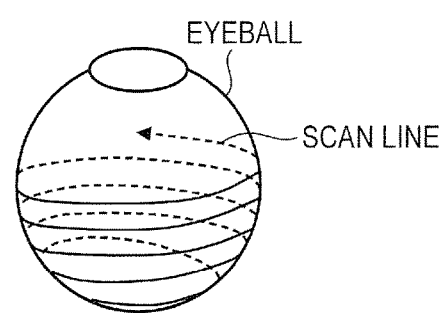

Moreover, in this embodiment, both of the X-axis scanner 53 and the Y-axis scanner 54 may be driven, and angles of the deflecting mirrors may be changed to scan with various types of irradiation light. For example, the raster scan as illustrated in FIG. 2A and FIG. 2B may be performed, or a method in which one point (for example, macula) of the eyeball is passed a plurality of times as illustrated in FIG. 2C may be performed. Moreover, scanning with the irradiation light may be performed spirally about one point (for example, macula) of the eyeball as illustrated in FIG. 2D.

Figure 3:
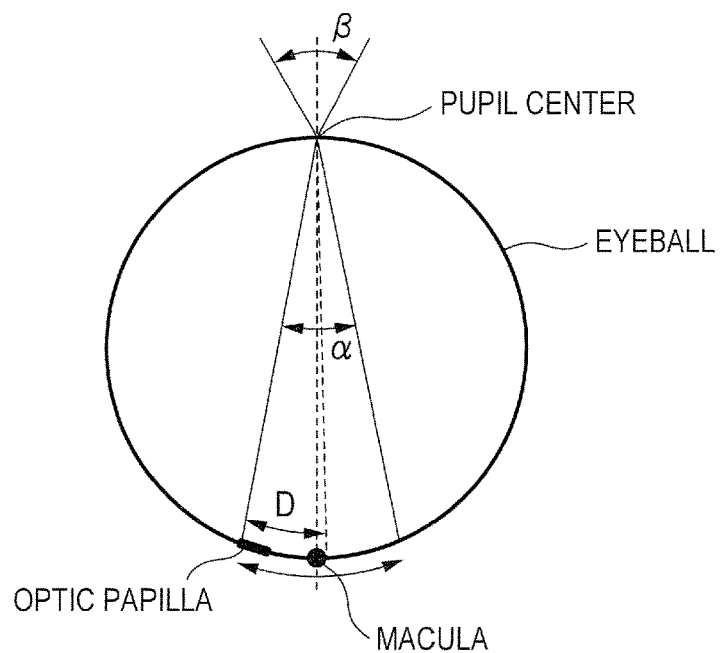
FIG. 3 is a schematic diagram of an eyeball.

Incidentally, in fundus inspection, there is a demand to acquire an image of the macula and an optic papilla in the same, that is, one scanning cycle. A range (scanning angle) scanned with the irradiation light of the OCT unit, which is required to realize the demand, is described with reference to FIG. 3. FIG. 3 is a schematic diagram in which the eyeball is assumed to be a sphere. On the opposite side of a pupil center of the eyeball, the macula is located. Moreover, at a small distance away from the macula, the optic papilla is located. The macula and the optic papilla are particularly important parts in the fundus.

In a fundus of a typical adult, a distance D encompassing the macula and the optic papilla is about 5.75 mm. The irradiation light is irradiated to the inside of a pupil of the eye to be inspected 100, and is rotated about the pupil center of the eyeball to scan the fundus. When an image is acquired over a range encompassing the optic papilla with the macula being at the center at once in the same scanning cycle, and individual differences are also taken into account, a length L of the shortest curve connecting the macula and the optic papilla (range of image acquisition) needs to be about 14 mm.

Here, an angle of deflection of the irradiation light (measurement light) rotated about the pupil center, which corresponds to the range of image acquisition, is represented by $\alpha$. An average diameter of an adult eyeball is about 24 mm, and hence in order to set the range of image acquisition L to 14 mm or larger, the angle of deflection $\alpha$ needs to be 33.4 degrees or higher. When the fact that an average refractive index in the eyeball is 1.38 is used, the angle when expressed as an angle of deflection $\beta$ of the irradiation light that enters the pupil center in the air is arcsin(1.38×sin(33.4 degrees/2))×2≈47 degrees.

In other words, when the fundus is linearly scanned with the irradiation light to acquire an image of the macula and the optic papilla at the same time under a state in which the macula is located at the center, an angular range in which the fundus is scanned only needs to be 47 degrees or larger in the air. Note that, in the following description, the air-equivalent range of the angular range in which the fundus is scanned when the fundus is linearly scanned with the irradiation light is defined as an "angle of view". That is, the angle of deflection $\beta$ is defined as the angle of view.

Figure 4:
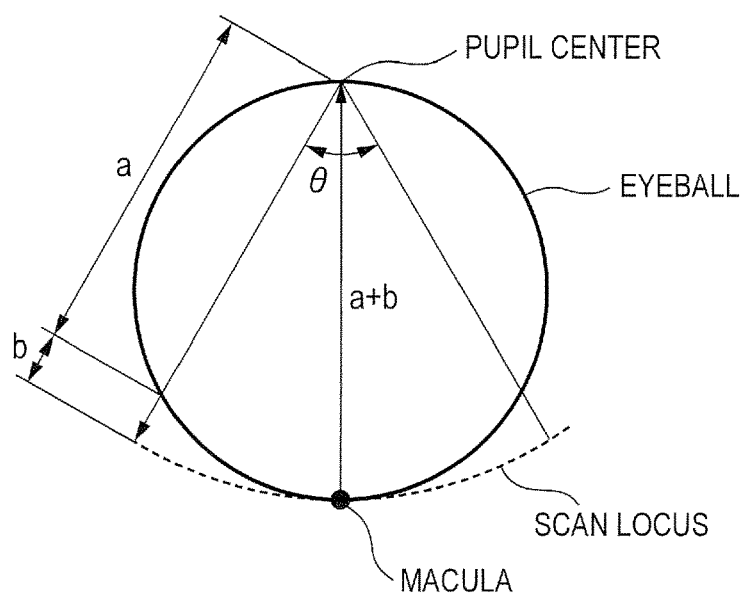
FIG. 4 is a diagram for illustrating a problem in realizing a wide angle of view.

Next, a problem that arises in the scanning at the above-mentioned angle of deflection $\beta$ is described with reference to FIG. 4. FIG. 4 is a schematic diagram of the eyeball that is assumed to be a sphere as in FIG. 3. The broken line illustrated in FIG. 4 indicates a scan locus of the irradiation light. As illustrated in FIG. 4, a physical distance from the pupil center to an outer wall, that is, the fundus, of the eyeball is a+b at the macula but is a in a portion at a position away from the macula (portion at an angle of θ/2). With the use of an axial length T of the eye and an angle of deflection θ in the eyeball, a and b are expressed as follows:

$$a = T \times \cos(\theta/2); \text{ and}$$

$$a + b = T$$

As can be seen, the distance from the pupil center to the macula and the distance from the pupil center to the position away from the macula are different by a distance b. The distance b becomes larger as the angle θ becomes larger. Therefore, in an OCT unit for fundus inspection having a wide angle of view, an optical path length from the pupil center to the macula and the distance from the pupil center to the peripheral position away from the macula greatly differ. The axial length T of an adult eye differs greatly with individuals, and the axial lengths T of eyes of 95% of adults fall within a range of 21 mm or more and 28 mm or less. In this example, as a value of the axial length T of the eye, the maximum value of 28 mm within the range is used, and when the angle of deflection θ in the eyeball is 33.4 degrees, b is about 1.2 mm according to Expressions 1 and 2.

Moreover, tissues of the fundus observed by the OCT unit for fundus inspection are the retina in the vicinity of the surface of the fundus and the choroid behind the retina. The retina is 0.50 mm thick at the thickest part, and the choroid is about 0.30 mm thick, with the result that the OCT unit for fundus inspection needs to acquire an image up to a depth of at least 0.80 mm. In other words, a difference in distance of 0.80 mm occurs between the surface of the fundus and the choroid.

Therefore, in order to acquire an image of the macula and the optic papilla in the same scanning cycle, and to obtain information on the vicinity of the surface of the optic papilla and the choroid behind the macula, data sampling under the following condition is required. That is, even when a difference in distance of 2×(b+0.80)≈4.0 mm occurs, obtaining a tomographic image without aliasing is required. This difference in distance corresponds to 4.0 mm×1.38≈5.5 mm in terms of a difference in optical path in the air. In other words, in order to realize the OCT unit capable of obtaining the information on the section even when the angle of view is 47 degrees or more, it is required that such high-speed data sampling that the tomographic image without aliasing is obtained even when there is a difference in optical path of 5.5 mm in the air be performed at equal wavenumber intervals.

When an image of the fundus is to be acquired over the wide angle of view, the angle of view is increased, and hence the number of tomographic images to be acquired also needs to be increased. In order to increase the number of images to be acquired, there is a need to perform the A-scan at high speed. A relationship between an A-scan rate fa and a sampling rate fs of an A/D converter is expressed, using the number of sampled data points Na per A-scan cycle, a ratio d of wavelength sweeping time in one A-scan cycle of the light source, a center wavelength λc of the light source, a swept wavelength band Δλ of the light source, and a depth range Δz in which the tomographic image is acquired, by the following expression.

$$f_s = \frac{N \times f_a}{d} = \frac{4\Delta z \times \Delta \lambda}{\lambda_c^2} \times \frac{f_a}{d}$$

For example, in order to realize a tomographic image at an image acquiring depth of 5.5 mm using a wavelength swept light source having a sweep frequency of 100 kHz, a ratio of wavelength sweep time of 50%, a center wavelength of 1,060 nm, and a swept wavelength band of 110 nm, when a distortion amount of wavelength sweep is ±20%, the sampling frequency is derived to be about 500 MHz. Therefore, the A/D converters are required to be capable of performing A/D conversion (sampling) at a frequency of about 500 MHz or higher. Moreover, in order to realize a wider angle of view and a higher speed of the A-scan in acquiring the fundus image, the sampling rate needs to be increased in proportion to an increase in A-scan rate. Then, there arises a need to use expensive A/D converters capable of performing high speed sampling. Moreover, simply using a plurality of A/D converters does not result in sampled data at the equal wavenumber intervals, and it is difficult to obtain a good tomographic image. This is taken into consideration in this embodiment, in which the plurality of A/D converters are used to perform data sampling of the interference signal, sampled data arrays of the A/D converters are integrated as equal wavenumber interval data, and the frequency analysis is performed to obtain a good tomographic image of the fundus.

Here, with substantially the same values as the above-mentioned center wavelength, wavelength width, image acquiring depth, and the like, and when the A-scan rate of the wavelength swept light source is about 300 kHz or higher, the sampling frequency is derived to be about 1.0 GHz or higher. At this time, a difference from frequencies that the A/D converters are capable of performing the A/D conversion (sampling) becomes significant, resulting in a situation in which application of this embodiment is more preferred. In other words, it is preferred that this embodiment be applied to a case where the A-scan rate of the wavelength swept light source, which is a speed at which light irradiated by the light source is frequency swept, is about 300 kHz or higher. Stated differently, it is preferred that this embodiment be applied to a case where a frequency at which the A/D converters need to sample is about 1.0 GHz or higher.

Figure 5:
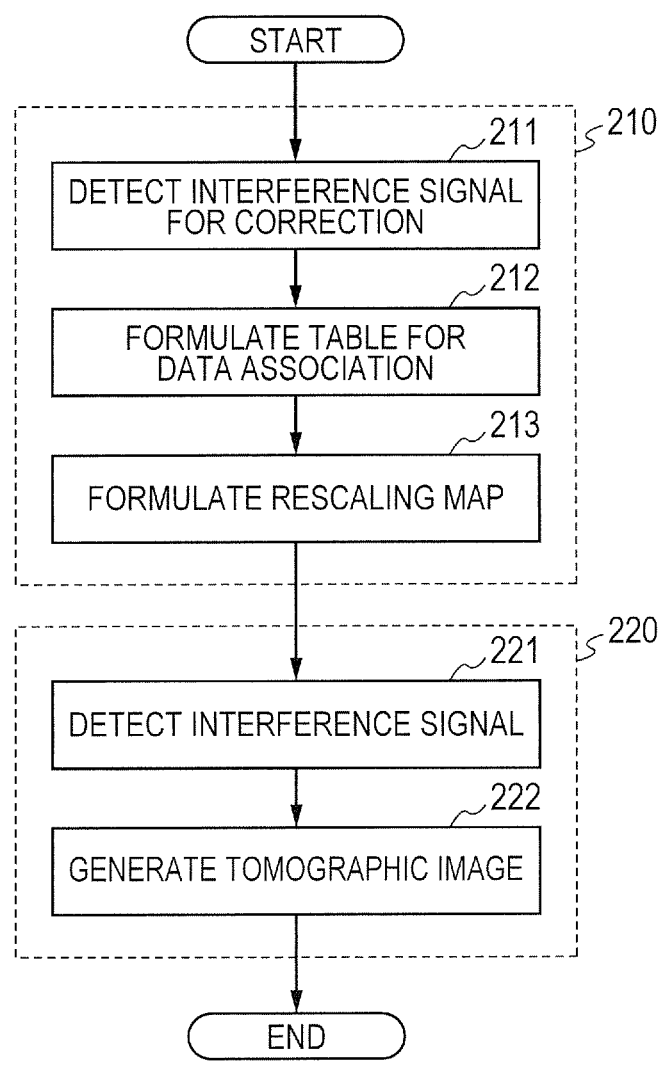
FIG. 5 is a chart for illustrating an overall flow from acquisition of data to generation of an image according to the first embodiment of the present invention.

Now, details of the processes executed in the first embodiment of the present invention are described. In FIG. 5, an overall flow of a process until the tomographic image of the eye to be inspected is generated is illustrated. In this embodiment, the generation of the tomographic image includes a process 210, which is a preliminary process, and a process 220, which is a main measurement process.

More specifically, the process 210 includes a process 211 of detecting coherent light for correction, a process 212 of associating data, and a process 213 of formulating a rescaling map. First, in the process 211, the information acquiring portion 40 receives a digital signal of the coherent light for correction transmitted from the detecting portion 30. As the coherent light for correction, coherent light obtained by using a mirror is used, for example. Next, in the process 212, in order to integrate data arrays of the digital signals acquired by the A/D converters 32a and 32b, the information acquiring portion 40 performs a process of associating indices of the data arrays. The process 212 is described later with reference to FIG. 6.

Finally, in the process 213, the information acquiring portion 40 formulates the rescaling map used to convert the digital signals into an equal wavenumber interval data array. The preliminary process 210 including the formulation of the rescaling map and the like is performed at the time when the OCT unit is started, or during maintenance of the OCT unit, which is performed after the elapse of a predetermined period, for example, and may be normally stored in a storage portion (not shown). During the main measurement, the rescaling map may be read and used as appropriate.

In the process 220, which is the main measurement, the tomographic image of the eye to be inspected 100 is generated. First, in a process 221, the detecting portion 30 detects the interference signal with the eye to be inspected 100 being an object to acquire an image. Next, in a process 222, the information acquiring portion 40 integrates the data arrays to be converted into an equal wavenumber interval data array, and uses the frequency analysis such as the Fourier transform to generate the tomographic image of the eye to be inspected 100.

Now, the above-mentioned process 212 is described in detail with reference to FIG. 6. In this process, for the interference signals sampled by the A/D converters 32a and 32b, an association table i'(j) for associating indices i and j of the data arrays is formulated. First, in a process 311, the information acquiring portion 40 acquires digital signal data arrays Ipre1(i) and Ipre2(j) respectively sampled by the A/D converter 32a and the A/D converter 32b.

Next, in a process 312, phase information Φpre1(i) and Φpre2(j) of data is extracted from the data arrays Ipre1(i) and Ipre2(j) of the interference signals. More specifically, phases are extracted by using the Hilbert transform and then the phases are connected to obtain Φpre1(i) and Φpre2(j) as a single phase data array that increases monotonously.

At this time, in order to correctly connect the phases, it is desired that a phase difference between two continuous points of sampled data Φ(i) and Φ(i+1) be less than 2π. For that end, a sampling frequency fs of the detecting portion 30 needs to be higher than a frequency f of the interference signal. In other words, in the preliminary process, a frequency of the interference signal for correction detected by the detecting portion 30 needs to be set lower than a detection frequency at which the detecting portion 30 actually detects the interference signal.

The phrase "frequency f of the interference signal" as used herein refers to a change with time of an interference spectrum detected by each of the A/D converters 32a and 32b. Therefore, a mirror is placed instead of the eye to be inspected 100 at a position at which a difference in optical path length ΔZ between the measurement arm 50 and the reference arm 60 satisfies the following expression to create the interference signal having a desired frequency.

$$\Delta Z < \frac{fs \times \lambda_i^2 \times d}{4\Delta\lambda \times f_a}$$

Then, in a process 313, the extracted phase data array Φpre1(i) is used to formulate a fitting function Φpre'1(i). Finally, in a process 314, the data number i' on the fitting function at which the phase Φpre2(j) of the j-th sampled data of the A/D converter 32b becomes Φpre2(j)=Φpre'1(i') is calculated. Then, the calculation result is stored as the table i'(j) for associating the index i and the index j in the information acquiring portion 40. This completes the formulation of the table for associating the indices of the data arrays sampled by the A/D converters 32a and 32b.

Next, the process 213 illustrated in FIG. 5 is described. In the process 213, the rescaling map is formulated. The rescaling map is a data array i"(k) that forms an equal wavenumber interval data array Ipre1(i"). Based on the data array Ipre1(i) of the interference signal acquired by the A/D converter 32a, i"(k) is calculated. First, the phase information Φpre1(i) of the digital signal of the A/D converter 32a, which is acquired in the process 312, is read. Next, i"(k) expressed as the following expression is acquired as the rescaling map.

$$i''(k) = \Phi_{pre1}^{-1}\left(\frac{\Delta\Phi \times (k-1) \times (N3-1)}{\Phi_{max}}\right)$$

In this expression, ΔΦ is a phase difference between continuous data points when the interference signal is resampled at the equal wavenumber intervals, Φmax is the maximum value of the phase data array, k=0 to N3−1, and N3 is the number of data points to be resampled. This completes the acquisition of the rescaling map.

The details of the preliminary process 210 have been described above. Next, details of the process 220, which is the main measurement process in which the tomographic image is actually generated, are described.

Figure 7:
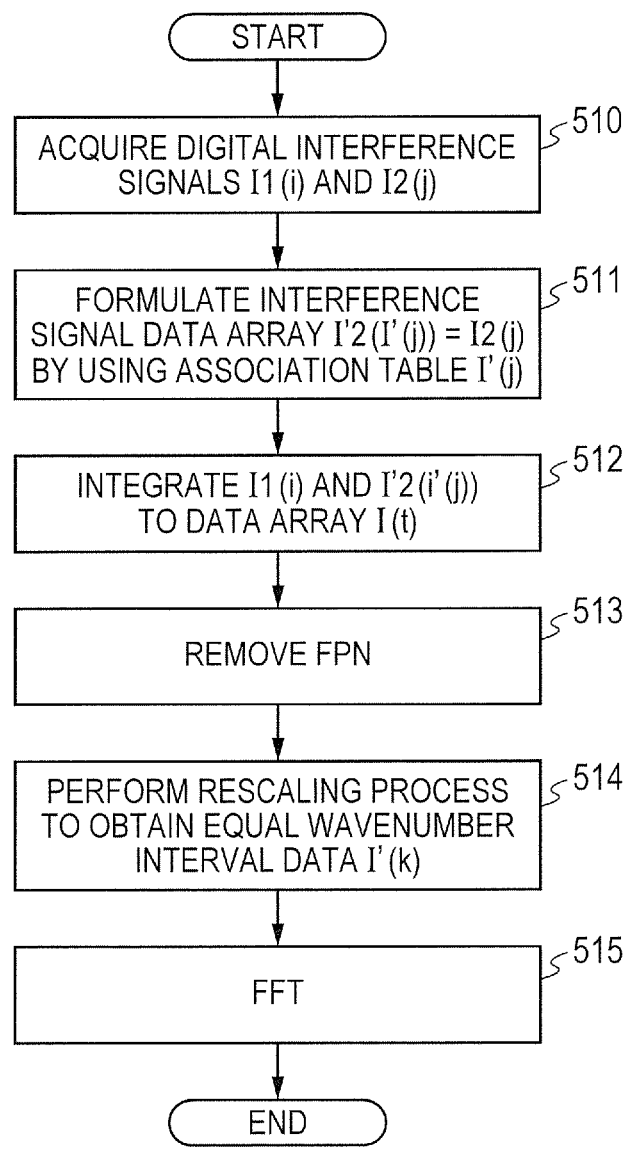
FIG. 7 is a flow chart for illustrating a process from measuring an object to be measured to acquiring a tomographic image.

In FIG. 7, details of the process 222, which is the process of generating the tomographic image in the process 220, are illustrated. First, in a process 510, the information acquiring portion 40 acquires digital interference signals I1(i) and I2(j), which have been detected by the detecting portion 30 through the respective A/D converters in the process 221, provided that i=0 to N1−1, and j=0 to N2−1. At this time, at an irradiation destination of the measurement arm 50, the eye to be inspected 100 of which the tomographic image is to be actually acquired is placed. Next, in a process 511, data numbers of the digital signal I2(j) acquired by the A/D converter 32b are renumbered. Using the index association table i'(j), which has been formulated in the process 212, a data array with which I'2(i'(j))=I2(j) is formulated.

Next, in a process 512, the data array I(t) obtained by integrating the interference signal data I1(i), which has been acquired by the A/D converter 32a, and the data I'2(i'(j)), which has been acquired by the A/D converter 32b and in which the data numbers have been renumbered, is formulated.

Then, in a process 513, fixed pattern noise (FPN) is removed. In the removal of the FPN, for example, spectral data acquired under a state in which there is no return light from the eye to be inspected 100 is subtracted from the interference signal I(t) to obtain I'(t) (t=0, N1+N2−1). The spectral data is obtained, more specifically, under a state in which irradiation of the measurement light on the eye to be inspected 100 is blocked by placing an obstruction between the focus lens 55 and the eye to be inspected 100.

After the removal of the FPN, in a process 514, a rescaling process is performed to obtain an equal wavenumber interval data array I'(k). More specifically, first, the i"(k)th numerical value in the digital signal I'(t) after the removal of the FPN, which has been determined in the process 513, is calculated based on known numerical values using 1D interpolation, spline interpolation, or the like. In order to improve interpolation accuracy in the rescaling process, before the interpolation calculation, FFT, zero padding, and inverse FFT may be performed on interference signal data I(t) in the stated order.

Finally, in a process 515, the FFT is performed on I'(k) to acquire the tomographic image. A mathematical compensation process and image correction may be performed before or after the process 515. Through the above-mentioned processes, the two data arrays obtained from the eye to be inspected 100 using the two A/D converters may be combined to obtain the single data array I(t). In this manner, the A-scan having a larger number of image acquisition points than that in a case where a single A/D converter is used may be performed.

In other words, according to the above-mentioned embodiment, the use of the plurality of A/D converters enables high-speed sampling. Moreover, the phase information of the interference signal is used to perform the index association and the rescaling process on the sampled data of each of the A/D converters, with the result that the equal wavenumber interval data array may be created. As a result, the good tomographic image may be obtained at a high A-scan rate, and even when the range of image acquisition in a single scanning cycle is increased, the information on the section may be acquired accurately.

Note that, the above-mentioned process 212 is executed by a data association unit, which is included in the information acquiring portion 40, and is configured to associate indices of at least two data arrays. In the association of the indices, the phase information of each data array is acquired by the data association unit, and the indices are associated based on the phase information. In this embodiment, the phase information is determined based on data arrays after transform, which are obtained by subjecting the data arrays to the Hilbert transform. The process 222, and more specifically, the process 512 are executed by an integration unit, which is included in the information acquiring portion 40, and is configured to integrate the at least two data arrays based on the associated indices, or on the acquired phase information. The rescaling process in the process 514 is executed by a rescaling unit, which is included in the information acquiring portion 40, and is configured to convert the integrated data array into the equal wavenumber interval data array. Further, the generation of the image in the process 222 is executed by an image generating unit, which is included in the information acquiring portion 40, and is configured to generate the tomographic image of the eye to be inspected based on the integrated data array.

Second Embodiment

Figure 8:
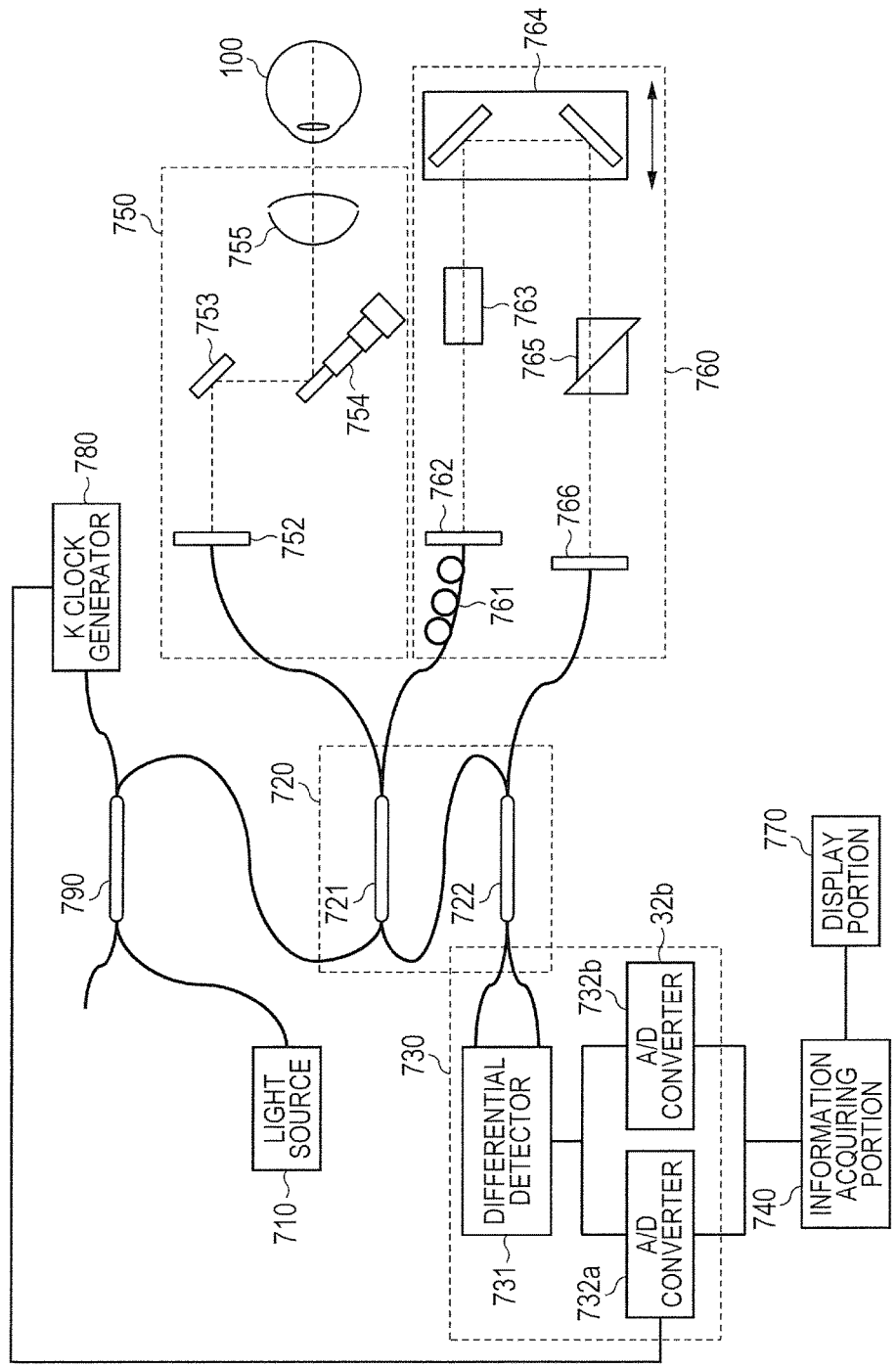
FIG. 8 is a schematic diagram for illustrating the schematic structure of an OCT unit according to a second embodiment of the present invention.

FIG. 8 is a schematic diagram for schematically illustrating a structure example of an imaging apparatus (OCT unit) employing optical coherence tomography according to a second embodiment of the present invention. Note that, the same components as those of the first embodiment are given the same name as in, for example, a light source 710, an interference unit 720, a detecting portion 730, an information acquiring portion 740, a measurement arm 750, and a reference arm 760, and a detailed description thereof is omitted here.

This second embodiment is different from the first embodiment in that a k clock generator 780 is included. The k clock generator 780 is provided so that an A/D converter 732a performs sampling at equal wavenumber intervals. In this embodiment, the A/D converter 732a performs the sampling at the equal wavenumber intervals, and hence the sampled data becomes a data array in which the phase is linearly increased. Therefore, in a fitting process using the phase information, which is to be described below, there is no need to perform higher-order fitting, and the need to formulate the rescaling map is eliminated, with the result that a computing load may be reduced.

The OCT unit according to this embodiment includes the light source 710, the interference unit 720, the detecting portion 730, the information acquiring portion 740, the measurement arm 750, and the reference arm 760. The OCT unit includes the light source 710 configured to irradiate light that is frequency swept, the interference unit 720 configured to generate coherent light, the detecting portion 730 configured to detect the coherent light, and the information acquiring portion 740 configured to acquire the information on the fundus of the eye to be inspected 100 based on the coherent light. The OCT unit also includes the measurement arm 750 and the reference arm 760.

A coupler 722 is configured to multiplex the reflected light from the eye to be inspected 100 that has passed through the measurement arm 750 and the light that has passed through the reference arm 760 to generate the coherent light. Then, the coherent light is detected by the detecting portion 730. The detecting portion 730 includes a differential detector 731, and an A/D converter 732a and an A/D converter 732b, which are analog-to-digital conversion units. In the detecting portion 730, each of the coherent light beams obtained by generating the coherent light in the coupler 722 and immediately thereafter demultiplexing the coherent light is detected by the differential detector 731. Then, an interference signal, which is converted into an electrical signal by photoelectric conversion performed by the differential detector 731, is diverged again, and the diverged signals are respectively converted into digital signals by the A/D converter 732a and the A/D converter 732b.

In the OCT unit in FIG. 8, sampling timings of the interference signal by the A/D converter 732a are at equal optical frequency (equal wavenumber) intervals based on k clock signals generated by the k clock generator 780 provided outside the light source 710. On the other hand, sampling timings of the A/D converter 732b are at the equal time intervals based on the internal clock included in the A/D converter. In order to diverge a part of light irradiated from the light source 710 to the k clock generator 780, a coupler 790 is provided. The k clock generator 780 and the coupler 790 may be incorporated in the light source 710.

Digital signals sampled by the respective A/D converters are transmitted to the information acquiring portion 740. The information acquiring portion 740 is configured to perform frequency analysis such as Fourier transform on those digital signals to obtain the information on the fundus. The obtained information on the fundus is displayed as a tomographic image by a display portion 770.

Now, details of the processes executed in the second embodiment of the present invention are described. In FIG. 9, an overall flow of a process until the tomographic image of the eye to be inspected is generated is illustrated. In this embodiment, the generation of the tomographic image includes a process 810, which is a preliminary process, and a process 820, which is a main measurement process.

More specifically, the process 810 includes a process 811 of detecting the coherent light for correction, and a process 812 of associating the indices of the data arrays sampled by the A/D converters. First, in the process 811, the detecting portion 730 detects an interference signal for correction for use in the process 812. As the coherent light for correction for obtaining the interference signal for correction, coherent light obtained by using a mirror is used, for example. Next, in the process 812, in order to integrate the data arrays of discrete interference signals sampled by the A/D converters 732a and 732b, the information acquiring portion 740 performs a process of associating indices of the data arrays.

The main measurement process 820, which is an image generation process, includes a process 821 of detecting the interference signal and a process 822 of generating the tomographic image. In the process 820, the acquisition of the interference signal with the eye to be inspected 100 being the object to acquire an image to the generation of an OCT image is performed. First, in the process 821, the detecting portion 730 detects the interference signal when the eye to be inspected 100 is the object to acquire an image. Next, in the process 822, the information acquiring portion 740 integrates the data arrays using a result of associating the indices, which is obtained in the preliminary process, to be converted into the equal wavenumber interval data array, and generates the OCT image of the eye to be inspected 100 using the frequency analysis such as the Fourier transform.

Figure 6:
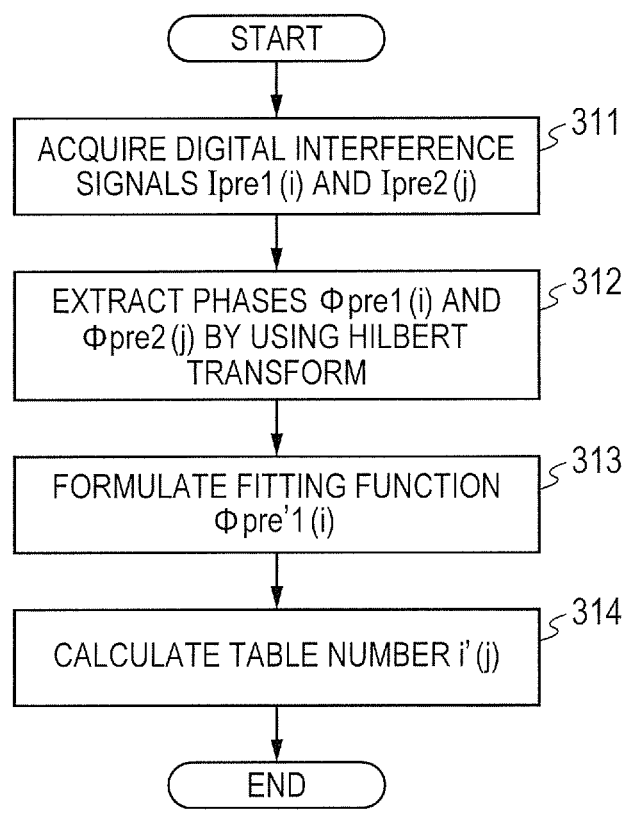
FIG. 6 is a flow chart for illustrating a process of associating indices of A/D converters, which is a preliminary process in the flow illustrated in FIG. 5.

The above-mentioned process 812 is similar to the process 212 in the first embodiment, and is illustrated in FIG. 6. In this process, for the interference signals sampled by the A/D converters 732a and 732b, the association table i'(j) for associating the indices i and j of the data arrays is formulated. First, in the process 811, the information acquiring portion 740 acquires a discrete interference signal data array Ipre1(i) sampled by the A/D converter 732a. On the other hand, in the process 311, the A/D converter 732b acquires a data array Ipre2(j) of the interference signal sampled at times different from those of the A/D converter 732a corresponding to the k clock signals.

Next, in the process 312, the phase information Φpre1(i) and Φpre2(j) of data is extracted from the data arrays Ipre1(i) and Ipre2(j) of the interference signals. More specifically, phases are extracted by using the Hilbert transform and then the phases are connected to obtain Φpre1(i) and Φpre2(j) as a single phase data array that increases monotonously.

Then, in the process 313, a fitting function Φ'pre1(i) is formulated using the extracted phase data array Φpre1(i). At this time, the A/D converter 732a performs sampling at the equal wavenumber intervals using the k clock signals generated by the k clock generator 780, and hence the fitting function Φ'pre1(i) becomes substantially linear.

Finally, in the process 314, the data number i' on the fitting function at which the phase Φpre2(j) of the j-th sampled data of the A/D converter 732b becomes Φpre2(j)=Φ'pre1(i') is calculated. Then, the calculation result is stored as the table i'(j) for associating the index i and the index j in the information acquiring portion 740. This completes the formulation of the table for associating the indices of the data arrays on the interference signals sampled by the A/D converters 732a and 732b.

The process 820 for the main measurement is similar to the process 220 in the first embodiment, and details of the process 822 of generating the tomographic image are illustrated in FIG. 7. The details are similar to those in the first embodiment, and hence a description thereof is omitted here.

FIGS. 10A and 10B are conceptual diagrams for illustrating details of the process 514 in the second embodiment. In FIG. 10A, the interference signal I(t) (t=0, N1+N2−1) obtained by the integration in the process 512 is illustrated, and in FIG. 10B, the interference signal I'(k) after the rescaling process in the process 514 is illustrated. The horizontal axis indicates the data numbers of the first A/D converter 732a, the vertical axis indicates the strength of the interference signal, the black circles indicate points sampled by the first A/D converter 732a, the white circles indicate points sampled by the second A/D converter 732b, and the wave line indicates cosine wave representing the interference signal in a single cycle, which is simplified for description.

In the actual processing, first, the number of data points N3 after the rescaling process is determined. As one example, in FIG. 10B, the number of data points is N3=2× N1, and a sampling interval is $\Delta t=0.5$. Next, numerical values of the white circles in FIG. 10B are calculated. More specifically, based on existing points of the white circles and the black circles in FIG. 10A, the numerical values are calculated using the 1D interpolation, the spline interpolation, or the like. In order to improve the interpolation accuracy in the rescaling process, before the interpolation calculation, the FFT, the zero padding, and the inverse FFT may be performed on the interference signal data I(t) in the stated order.

The above-mentioned processes may be performed to integrate the data arrays obtained by different A/D converters without formulating the rescaling map. As a result, the high speed sampling may be enabled, the good tomographic image may be obtained with the high A-scan rate, and even when the range of image acquisition in one scanning cycle is increased, the information on the section may be acquired accurately.

Note that, in the above-mentioned embodiments, two A/D converters (analog-to-digital converters) are used, but the number may be more than two. Moreover, when the number of A/D converters is increased, it is preferred to provide a plurality of phase difference generating units so that respective phases are shifted. Each of the phase difference generating units included in the detecting portion gives a phase difference to each data array, and the phase difference gives a difference in index among the data arrays. Alternatively, in the case of the second embodiment, it is preferred to provide the k clock generator so that the data array obtained by at least one of at least two A/D converters is sampled at the equal wavenumber intervals. Moreover, in this case, it is preferred that the other of the at least two A/D converters supply an equal time interval data array.

Other Embodiments

Note that, the present invention is not limited to the above-mentioned embodiments, and may be conducted with various changes and modifications within the scope that does not depart from the gist of the present invention. For example, in the above-mentioned embodiments, the imaging apparatus and the method of operating the imaging apparatus are exemplified as subjects to which the present invention is applied. However, embodiment modes of an information processing apparatus to be communicably connected to the imaging apparatus, which includes an optical system, the interference unit, the A/D converters, and the like, and which is configured to generate and integrate the data arrays to generate an image, or a method of operating the information processing apparatus are also possible. Further, the description of the above-mentioned embodiments is directed to the case where an object to be inspected is a fundus of an eye to be inspected, but the present invention may be applied to an object to be inspected such as a skin or an organ other than the eye. In this case, the present invention has a mode as medical equipment such as an endoscope other than an ophthalmologic apparatus. Accordingly, it is desired that the present invention be grasped as an imaging apparatus for use in an inspection apparatus exemplified by the ophthalmologic apparatus, and the eye to be inspected be grasped as one mode of the object to be inspected.

Moreover, embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-093998, filed May 1, 2015, which is hereby incorporated by reference herein in its entirety.

What is claimed is:
1. An imaging apparatus, comprising:
a light source configured to irradiate light that is frequency swept;
an interference unit configured to diverge the irradiation light into irradiation light, which is to be irradiated on an object to be inspected, and reference light, to gen- erate coherent light from reflected light of the irradiation light from the object to be inspected and the reference light;

at least two conversion units configured to subject at least two analog signals, which are obtained by diverging an analog signal of the coherent light, to analog-to-digital conversion;

an association unit configured to associate indices of at least two data arrays obtained by the analog-to-digital conversion;

an integration unit configured to integrate the at least two data arrays based on the associated indices; and an image generating unit configured to generate an image of the object to be inspected based on a data array obtained by the integration.

2. An imaging apparatus according to claim 1, wherein the association unit is configured to acquire phase information of each of the at least two data arrays, and associate the indices of the at least two data arrays based on the acquired phase information.

3. An imaging apparatus according to claim 2, wherein the association unit is configured to subject each of the at least two data arrays to Hilbert transform, and acquire the phase information from each of the at least two data arrays that have been subjected to the Hilbert transform.

4. An imaging apparatus according to claim 1, wherein the association unit is used in a preliminary process before a process in which the image of the object to be inspected is acquired, and wherein, in the preliminary process, a frequency of the analog signal obtained from interference light for correction is lower than a detection frequency at which the data array is detected.

5. An imaging apparatus according to claim 1, further comprising a k clock generator configured to generate a clock signal for subjecting the analog signal, which is to be transmitted to at least one conversion unit of the at least two conversion units, to analog-to-digital conversion at equal wavenumber intervals, wherein at least another one of the at least two conversion units is an analog-to-digital conversion unit configured to perform analog-to-digital conversion at equal time intervals.

6. An imaging apparatus, comprising:

a light source configured to irradiate light that is frequency swept;

an interference unit configured to diverge the irradiation light into irradiation light, which is to be irradiated on an object to be inspected, and reference light, to generate coherent light from reflected light of the irradiation light from the object to be inspected and the reference light;

at least two analog-to-digital conversion units configured to subject at least two analog signals, which are obtained by diverging an analog signal of the coherent light, to analog-to-digital conversion;

an integration unit configured to integrate at least two data arrays obtained by the analog-to-digital conversion based on phase information of the at least two data arrays; and an image generating unit configured to generate an image of the object to be inspected based on a data array obtained by the integration.

7. An imaging apparatus according to claim 6, further comprising an association unit configured to associate the at least two data arrays based on phase information of each of the at least two data arrays, wherein the integration unit is configured to integrate the associated at least two data arrays.

8. An imaging apparatus according to claim 6, further comprising a phase difference generating unit configured to give a phase difference to the at least two data arrays, wherein the phase difference gives a difference to phase information of each of the at least two data arrays.

9. An imaging apparatus according to claim 6, further comprising a rescaling unit configured to convert the data array obtained by the integration into an equal wavenumber interval data array, wherein the image generating unit is configured to generate the image of the object to be inspected using the equal wavenumber interval data array.

10. An imaging apparatus according to claim 6, further comprising a k clock generator configured to generate a clock signal for making, in detecting at least one data array of the at least two data arrays, the at least one data array an equal wavenumber interval data array, wherein another data array of the at least two data arrays is an equal time interval data array.

11. An imaging apparatus according to claim 6, wherein the at least two analog-to-digital conversion units perform the analog-to-digital conversion at equal time intervals.

12. An imaging apparatus according to claim 1, wherein an A-scan rate, which is a speed at which the light irradiated by the light source is frequency swept, is 300 kHz or higher.

13. An imaging apparatus according to claim 1, wherein a frequency at which the at least two conversion units sample is 1.0 GHz or higher.

14. An information processing apparatus, which is to be communicably connected to an imaging apparatus, the imaging apparatus comprising:

a light source configured to irradiate light that is frequency swept;

an interference unit configured to diverge the irradiation light into irradiation light, which is to be irradiated on an object to be inspected, and reference light, to generate coherent light from reflected light of the irradiation light from the object to be inspected and the reference light; and at least two conversion units configured to subject at least two analog signals, which are obtained by diverging an analog signal of the coherent light, to analog-to-digital conversion, the information processing apparatus comprising:

an association unit configured to associate indices of at least two data arrays obtained by the analog-to-digital conversion;

an integration unit configured to integrate the at least two data arrays based on the associated indices; and an image generating unit configured to generate an image of the object to be inspected based on a data array obtained by the integration.

15. An information processing apparatus, which is to be communicably connected to an imaging apparatus, the imaging apparatus comprising:

a light source configured to irradiate light that is frequency swept;

an interference unit configured to diverge the irradiation light into irradiation light, which is to be irradiated on an object to be inspected, and reference light, to generate coherent light from reflected light of the irradiation light from the object to be inspected and the reference light; and at least two conversion units configured to subject at least two analog signals, which are obtained by diverging an analog signal of the coherent light, to analog-to-digital conversion, the information processing apparatus comprising:

an integration unit configured to integrate at least two data arrays obtained by the analog-to-digital conversion based on phase information of the at least two data arrays; and an image generating unit configured to generate an image of the object to be inspected based on a data array obtained by the integration.

16. An information processing apparatus according to claim 15, further comprising an association unit configured to associate the at least two data arrays based on phase information of each of the at least two data arrays, wherein the integration unit is configured to integrate the associated at least two data arrays.

17. A method of operating an imaging apparatus, the imaging apparatus comprising:

a light source configured to irradiate light that is frequency swept;

an interference unit configured to diverge the irradiation light into irradiation light, which is to be irradiated on an object to be inspected, and reference light, to generate coherent light from reflected light of the irradiation light from the object to be inspected and the reference light; and at least two conversion units configured to subject at least two analog signals, which are obtained by diverging an analog signal of the coherent light, to analog-to-digital conversion, the method comprising:

associating indices of at least two data arrays obtained by the analog-to-digital conversion;

integrating the at least two data arrays based on the associated indices; and generating an image of the object to be inspected based on a data array obtained by the integration.

18. A method of operating an imaging apparatus, the imaging apparatus comprising:

a light source configured to irradiate light that is frequency swept;

an interference unit configured to diverge the irradiation light into irradiation light, which is to be irradiated on an object to be inspected, and reference light, to generate coherent light from reflected light of the irradiation light from the object to be inspected and the reference light; and at least two conversion units configured to subject at least two analog signals, which are obtained by diverging an analog signal of the coherent light, to analog-to-digital conversion, the method comprising:

integrating at least two data arrays obtained by the analog-to-digital conversion based on the phase information of the at least two data arrays; and generating an image of the object to be inspected based on a data array obtained by the integration.

19. A non-transitory computer-readable storage medium having stored thereon a program for causing a computer to execute the method of operating an imaging apparatus of claim 17.

20. A non-transitory computer-readable storage medium having stored thereon a program for causing a computer to execute the method of operating an imaging apparatus of claim 18.

* * * * *